US009968614B2

(12) United States Patent
Hingorani et al.

(10) Patent No.: US 9,968,614 B2
(45) Date of Patent: May 15, 2018

(54) APREPITANT INJECTABLE FORMULATIONS

(71) Applicant: InnoPharma, Inc., New York, NY (US)

(72) Inventors: Tushar Hingorani, Piscataway, NJ (US); Kumaresh Soppimath, Monmouth Junction, NJ (US); Satish Pejaver, Bridgewater, NJ (US); Navneet Puri, Bridgewater, NJ (US)

(73) Assignee: InnoPharma, Inc., Piscataway, NJ (US)

( * ) Notice: Subject to any disclaimer, the term of this patent is extended or adjusted under 35 U.S.C. 154(b) by 0 days. days.

(21) Appl. No.: 15/419,191

(22) Filed: Jan. 30, 2017

(65) Prior Publication Data

US 2017/0136027 A1 May 18, 2017

Related U.S. Application Data

(63) Continuation of application No. 13/901,978, filed on May 24, 2013, now abandoned.

(60) Provisional application No. 61/651,501, filed on May 24, 2012, provisional application No. 61/798,276, filed on Mar. 15, 2013.

(51) Int. Cl.
*A61K 31/5377* (2006.01)
*A61K 9/00* (2006.01)
*A61K 47/26* (2006.01)
*A61K 9/08* (2006.01)
*A61K 47/10* (2017.01)

(52) U.S. Cl.
CPC ........ *A61K 31/5377* (2013.01); *A61K 9/0019* (2013.01); *A61K 9/08* (2013.01); *A61K 47/10* (2013.01); *A61K 47/26* (2013.01)

(58) Field of Classification Search
None
See application file for complete search history.

(56) References Cited

U.S. PATENT DOCUMENTS

| 8,133,994 | B2 | 3/2012 | Vankawala et al. |
| 8,435,970 | B2 | 5/2013 | Curry et al. |
| 2009/0209541 | A1 | 8/2009 | Jain et al. |
| 2010/0151035 | A1 | 6/2010 | Ramaswami et al. |
| 2011/0009362 | A1 | 1/2011 | Joshi et al. |
| 2011/0015191 | A1 | 1/2011 | Ludescher et al. |
| 2011/0094321 | A1 | 4/2011 | Vankawala et al. |
| 2012/0277426 | A1 | 11/2012 | Jain et al. |

FOREIGN PATENT DOCUMENTS

| CN | 102379845 A | 3/2012 |
| WO | 2007088483 A1 | 8/2007 |
| WO | 2007112457 A2 | 10/2007 |
| WO | 2007147160 A2 | 12/2007 |
| WO | 2009108828 A2 | 9/2009 |
| WO | 2011158053 A1 | 12/2011 |
| WO | 2011161531 A1 | 12/2011 |

OTHER PUBLICATIONS

ISA/US, International Search Report and Written Opinion for International Application No. PCT/US13/042618.

*Primary Examiner* — Ernst V Arnold
*Assistant Examiner* — Kyung S Chang
(74) *Attorney, Agent, or Firm* — Jason G. Tebbutt

(57) ABSTRACT

An aqueous stable and ready-to-use formulation of aprepitant is prepared. Especially preferred formulations comprise a synergistic combination of a co-solvent and a surfactant and may further include a secondary co-solvent. Among other advantages of contemplated formulations, aprepitant is dissolved at high concentrations and remains dissolved and stable, even over prolonged periods of time.

15 Claims, No Drawings

APREPITANT INJECTABLE FORMULATIONS

This application claims priority to U.S. provisional application having Ser. No. 61/651,501, which was filed May 24, 2012, and to U.S. provisional application having Ser. No. 61/798,276, which was filed Mar. 15, 2013, both incorporated by reference herein.

FIELD THE INVENTION

The field of the invention is parenteral, and especially injectable dosage forms for the administration of aprepitant to an individual. In especially preferred dosage forms, aprepitant is in a stable and dissolved form.

BACKGROUND

Aprepitant (5-([(2R,3S)-2((R)-1-[3,5-bis(trifluoromethyl) phenyl]ethoxy)-3-(4-fluoro-phenyl)morpholino]methyl)-1H-1,2,4-triazol-3(2H)-one) is an antiemetic compound that belongs to the class of substance P antagonists that mediate their effect by blocking the neurokinin (NK1) receptor. Aprepitant is a selective, high-affinity antagonist at human substance P NK-1 receptors and is manufactured by Merck & Co. (available under the brand name, Emend®). It is available as oral capsules for the prevention and control of acute and delayed chemotherapy induced nausea and vomiting and for prevention of postoperative nausea and vomiting.

Aprepitant is a white to off-white crystalline, solid, with a molecular weight of 534.43 with structure:

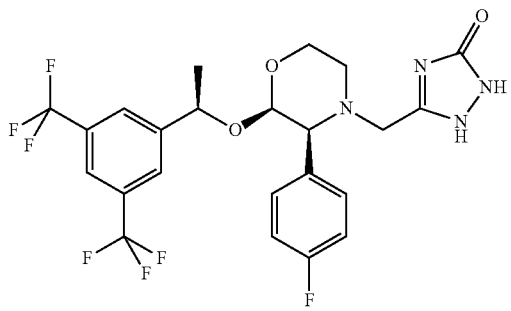 [SMILES: C[C@@H](O[C@H]1OCCN(Cc2nc(=O)[nH][nH]2)[C@H]1c1ccc(F)cc1)c1cc(C(F)(F)F)cc(C(F)(F)F)c1]

Aprepitant is practically insoluble in water, sparingly soluble in ethanol and isopropyl acetate, and slightly soluble in acetonitrile. Typical solubility data of Aprepitant using ethanol as a solvent (with the balance water) are shown in Table 1 below. As can be seen from the table, pharmaceutically relevant concentrations are typically only achieved at unacceptably high ethanol concentrations.

TABLE 1

| Ethanol Conc. (v/v) | Aprepitant Conc. (mg/mL) |
| --- | --- |
| 10 | 0.0001 |
| 30 | 0.0232 |
| 50 | 1.76 |
| 55 | 3.30 |
| 60 | 5.1 |
| 70 | 12.8 |
| 90 | 21.8 |

To overcome problems associated with poor solubility of aprepitant in pharmaceutical compositions, oral formulations of aprepitant can be prepared and are commercially available as a nanoparticulate composition (EMEND™, Merck) with an average particle size of less than about 1000 nm. However, the bioavailability of the compound when given orally is only about 60-65%.

Several attempts were made to solubility the aprepitant by solid-state manipulation. For example, WO 2007/088483 describes the preparation of amorphous aprepitant, while WO 2007/112457 discloses a mixture of two crystalline forms, namely, Form I and Form II, and pharmaceutical compositions thereof. US 2010/0151035 discloses a pharmaceutical composition of aprepitant containing a polymer and inert, pellets, whereby the dissolution rate of the drug is dependent on particle size of pellets. WO 2007/147160 describes compositions of amorphous aprepitant in the form of a co-precipitate with enhanced solubility of aprepitant, and US 2011/0009362 discloses a solubility enhanced form of aprepitant that involves forming a co-precipitate between the drug and cyclodextrin. However, the stability of such compositions in solution is generally insufficient. These and all other extrinsic materials discussed herein are incorporated herein by reference in their entirety. Where a definition or use of a term in an incorporated reference is inconsistent or contrary to the definition of that term provided herein, the definition of that term provided herein applies and the definition of that term in the reference does not apply. However, notwithstanding numerous attempts to increase the solubility of aprepitant, aprepitant per se is available only in a formulation for oral administration.

Aprepitant is also available as a water soluble prodrug salt form (e.g., EMEND™ for injection, Merck), fosaprepitant dimeglumine, for intravenous (IV) administration since aprepitant by itself has limited water solubility. Fosaprepitant is a phosphorylated prodrug form of aprepitant and is rapidly converted to aprepitant after IV administration. Prodrug formation of aprepitant molecule involves phosphorylation of the aprepitant molecule followed by salt formation with dimeglumine. Fosaprepitant has been reported to undergo rapid conversion to aprepitant in less than 30 minutes of an IV infusion. Studies have shown the non-inferiority and bioequivalency of fosaprepitant to aprepitant with respect to the prevention and control of acute and delayed chemotherapy induced nausea and vomiting. However, the additional steps required for the synthesis of fosaprepitant add significant complexity and cost to the drug. Furthermore, the commercial formulation of the prodrug of aprepitant, Emend® is reported to be stable only for 24 hours after reconstitution.

In view of the fact that fosaprepitant rapidly converts to the active form in vivo, it would certainly be advantageous from a manufacturing, use, and cost standpoint to formulate aprepitant in a soluble and stable form for parenteral administration. However, and to the best of the inventors' knowledge, no such soluble and stable formulation of aprepitant has been reported. Thus, there is a need for a stable liquid formulation of aprepitant for parenteral delivery.

SUMMARY OF THE INVENTION

The inventive subject matter is drawn to compositions, methods, and formulations of aprepitant in which aprepitant is present in a stable liquid formulation that is either ready-to-use or a concentrate ready for dilution in a suitable diluent, preferably for injection using an intravenous, an intramuscular, or a subcutaneous route. The formulations presented herein have a relatively high water content and exhibit remarkable storage stability.

In one embodiment of the inventive subject matter, a sterile liquid formulation of aprepitant for injection comprises an aqueous single phase solvent system that comprises water, a primary co-solvent (an in selected embodiments the primary co-solvent without water), a surfactant, and a secondary co-solvent, wherein the primary co-solvent and the surfactant are present in a synergistic ratio with respect to the solubilization of aprepitant, wherein the secondary co-solvent is present in an amount of equal or less than 6 volume % of the water and the primary co-solvent together, and wherein aprepitant is present in the sterile liquid formulation at a concentration of at least 2 mg/ml, and more typically at least 5 mg/ml.

In the sterile liquid formulation of aprepitant, the primary co-solvent is a short-chain alcohol, for example ethanol, while the surfactants are nonionic surfactants, a polysorbate, etc. The secondary co-solvent is a short-chain polyethylene glycol (typically present at equal or less than 3 volume %), or dimethylacetamide (typically present at equal or less than 1 vol %). In an embodiment, the formulation comprises ethanol as the primary co-solvent, a short-chain polyethylene glycol or dimethylacetamide as the secondary co-solvent, and a polysorbate (e.g., polysorbate 80) as the surfactant. In an embodiment, the secondary co-solvent may be omitted from the sterile liquid formulation.

In yet another embodiment of the inventive subject matter, disclosed herein is a kit for the preparation of a sterile liquid formulation of aprepitant for injection. In an embodiment, the kit will comprise (a) a first container that includes a non-aqueous solvent system comprising a primary co-solvent, a surfactant, and an optional secondary co-solvent, wherein the primary co-solvent and the surfactant are present in a synergistic ratio with respect to solubilization of aprepitant, wherein the optional secondary co-solvent is present in an amount equal or less than 30 volume % of the primary co-solvent and the surfactant together, and wherein aprepitant is present at a concentration of at least 9 mg/ml; and (b) a second container that includes a sterile aqueous diluent in an amount sufficient to dilute the aprepitant to a concentration of at least 5 mg/ml, wherein the non-aqueous solvent system and the sterile aqueous diluent are present in an amount such that the aprepitant at a concentration of at, least 2 mg/ml, and more typically at least 5 mg/ml, is completely soluble and stable in the sterile liquid formulation.

In an embodiment, the primary co-solvent is a short-chain alcohol, the surfactant is a non-ionic surfactant, and/or the secondary co-solvent, is a short-chain polyethylene glycol or dimethylacetamide. In an embodiment the sterile aqueous diluent is water. Such kits will allow for the formulation of an aqueous, ready-to-use formulation of aprepitant in which the aprepitant remains in solution upon dilution with an aqueous diluent. Moreover, it should be noted that aprepitant in the formulations presented herein has significant stability, even upon prolonged storage in liquid form.

Therefore, and viewed from a different perspective, disclosed herein is a method of increasing solubility and stability of aprepitant in an aqueous solution. In an embodiment the formulation step comprises preparation of an aqueous single phase solvent system comprising water, a primary co-solvent, and a surfactant, wherein the primary co-solvent and the surfactant, are present in a synergistic ratio with respect to solubilization of aprepitant. In an embodiment, aprepitant is dissolved in a secondary co-solvent to form a concentrated aprepitant solution, and in yet another embodiment, the concentrated aprepitant solution is combined with the aqueous single phase solvent system to form an aprepitant formulation that provides increased solubility and stability for aprepitant.

In an embodiment, the primary co-solvent is a short-chain alcohol, and/or the surfactant is a nonionic surfactant, and/or the secondary co-solvent is a short-chain polyethylene glycol or dimethylacetamide. In another embodiment, the aprepitant formulation contains at least 5 mg/ml aprepitant, and the aprepitant in the formulation is chemically stable and remains in solution for at least one month when stored at 40° C. and 75% relative humidity.

Various objects, features, aspects and advantages of the inventive subject matter will become more apparent from the following detailed description of preferred embodiments.

DETAILED DESCRIPTION

The inventors have discovered that liquid aprepitant formulations can be prepared in an entirely solubilized and stable form suitable for injection. The sterile liquid formulation of aprepitant disclosed herein have a relatively high water content and exhibit remarkable storage stability. Contemplated solutions can be prepared as concentrates that are diluted with a suitable diluent prior to use, for example, within 24 hours of use, or can be prepared as a ready-to-use sterile solution that can be used for injection without dilution.

In one especially preferred aspect of the inventive subject matter, the inventors have discovered that aprepitant solutions can be prepared in which aprepitant is not only soluble at pharmaceutically useful concentration, but also stable (i.e., remains chemically unchanged) over significant periods of time. Moreover, the solvents used in the compositions and methods according to the inventive subject matter are suitable for injection.

More specifically, the inventors have discovered that the solubility and stability of aprepitant in an aqueous solution can be significantly increased over heretofore known formulations by preparing an aqueous single phase solvent system that includes water, a primary co-solvent, and a surfactant. The inventors unexpectedly found that the primary co-solvent and the surfactant can be combined to provide a synergistic mixture for solubilization of aprepitant, i.e., the solvent mixture solubilizes aprepitant in a quantity that is higher than the solubilization of aprepitant in the primary co-solvent and surfactant alone. Solubility of aprepitant in the final product can be even further increased by pre-dissolution of aprepitant in a secondary co-solvent to form a concentrated aprepitant solution, which is then combined with the aqueous single phase solvent system. Aprepitant can be solubilized in the final product to a concentration of at least 2 mg/ml, more typically at a concentration of at least 3-4 mg/ml, and even more typically at a concentration of at least 5 mg/ml. While such high concentrations are typically only achieved by using unacceptably high quantities of a primary co-solvent (e.g., 60 volume % ethanol), or a surfactant (e.g., 30 w/v % polysorbate 80), the compositions of the sterile liquid formulation of aprepitant will typically have a significantly lower concentrations of primary co-solvent (e.g., about 30 vol % ethanol) and surfactant (e.g., about 1.5 w/v % polysorbate 80). In an embodiment, the aprepitant in the sterile liquid formulation of aprepitant remain dissolved and stable over several weeks, and even months at storage at 40° C. and 75% relative humidity. Such finding is particularly remarkable as many of the formulations presented herein have substantial quantities of water (either with water in the original formulation or after dilution with aqueous diluent).

In particularly preferred aspects, the primary co-solvent is a short-chain alcohol (i.e., less than 6 carbon atoms), and especially ethanol. However, it should be appreciated that numerous other solvents are also contemplated herein, and exemplary alternative solvents include pharmaceutically acceptable non-aqueous solvents, which may be polar or non-polar, protic or aprotic. For example, and among other solvents, contemplated solvents include linear and branched hydrocarbons, dioxane, ethyl acetate, propylene carbonate, dimethyl sulfoxide, short-chain alcohols, acetic acid, etc. Moreover, it should be noted that the primary co-solvent may be combined with one or more other co-solvents to so form a solvent mixture. In especially preferred aspects, the primary co-solvent is in admixture with water or saline to so form an, aqueous solvent system. While not limiting to the inventive subject matter, it is generally preferred that the water and primary co-solvent (and secondary co-solvent and/or surfactant) form a single phase solvent: system. However, in certain alternative aspects, emulsions and other multi-phase solvent systems are also deemed suitable for use herein. Most typically, the primary co-solvent and water will form the predominant fraction of the final formulation and will, for example, make up between 51-60 vol %, between 61-70 vol %, between 61-70 vol %, between 71-80 vol %, between 81-90 vol %, and in certain cases between 91-99 vol % (and even higher).

Particularly preferred surfactants include pharmaceutically acceptable surfactants, and all surfactants are generally contemplated herein. However, it is particularly preferred that the surfactant is a nonionic or zwitterionic (neutrally charged at physiological pH) surfactant. Therefore, especially preferred surfactants include polyoxyethylene glycol alkyl ethers, polyoxypropylene glycol alkyl ethers, glucoside alkyl ethers, polyoxyethylene glycol octylphenol ethers, polyethylene glycol ethers, polyethylene glycol esters, glycerol alkyl esters, polyoxyethylene glycol sorbitan alkyl esters, sorbitan alkyl esters, cocamide MEA, cocamide DEA, poloxamers, etc.

In less preferred aspects, the surfactant may be cationic and comprise a quaternary ammonium group (e.g., cetyltrimethylammonium bromide) or form an amine salt (e.g. octadecylamine hydrochloride), or the surfactant may be anionic (e.g., sodium/potassium stearate, sodium dioctylsulphosuccinate, sodium dodecylbenzenesulphonate, sodium lauryl sulphate, etc.). Alternatively, naturally occurring surface active agents may be used and include various phospholipids, e.g. diacylphosphatidyl glycerols, diaceylphosphatidyl cholines, and diaceylphosphatidic acids, the precursors and derivatives thereof, such as for example soybean lecithin and egg yolk, etc.

It is particularly preferred that the surfactant will be able to form with the primary co-solvent in water a synergistic combination with respect to solubilication of aprepitant, typically in a synergistic ratio in which the primary co-solvent is present in, a quantity that is larger than the surfactant. Therefore, contemplated synergistic ratios of primary co-solvent to surfactants will be between 2:1 and 5:1, between 5:1 and 10:1, between 10:1 and 20:1, between 20:1 and 40:1, or between 40:1 and 100:1. For example where the primary co-solvent is ethanol, and the surfactant is polysorbate 80, suitable ratios will be between 4:1 and 15:1, between 15:1 and 25:1, or between 25:1 and 60:1. Consequently, it should be appreciated that the surfactant will present a minor component of the final composition, typically in quantities of between about 0.1-1.0 w/v %, or between about 1.0-3.0 w/v %, or between about 3-5 w/v % (and in some cases even higher).

With respect to suitable secondary co-solvents it is generally contemplated that the secondary co-solvent is miscible, with the water and primary co-solvent without formation of a distinct phase in the quantities used, and/or that the secondary co-solvent will be able to completely dissolve aprepitant at relatively high concentrations (e.g., at least at 1 mg/ml, in an embodiment at least 10 mg/ml, in another embodiment at least 50 mg/ml, and in yet another embodiment at least 100 mg/ml). Therefore, especially suitable secondary co-solvents include tetraglycol, dimethylacetamide, short-chain polyethylene glycol (typically having an average molecular weight of less than 2,000, in an embodiment less than 1,000, and in yet another embodiment less than 500), NMP (N-methylpyrrolidone), propylene glycol, vitamin F: TPGS, benzyl alcohol, ethanol, etc. The secondary co-solvent will form a minor fraction of the final formulation and will, for example, make up between 49-40 vol %, between 39-30 vol %, between 29-20 vol %, between 19-10 vol %, between 9-1 vol %, and in certain cases between 1-0.09 vol % (and even less). Therefore, in an example of the formulations, the secondary co-solvent may be present in an amount of equal or less than 30 vol %, equal or less than 10 vol %, in an embodiment equal or less than 6 volume %, in another embodiment equal or less than 3 volume %, and in yet another embodiment equal or less than 1 volume % of the water and the primary co-solvent together. In an embodiment of the formulations, the secondary co-solvent may also be entirely omitted from the sterile liquid formulation.

Liquid aprepitant-containing formulation disclosed herein may further include various other excipients to maintain or increase drug stability. Such excipients may include buffer(s), antioxidant(s), chelating agent(s), etc. if required, the composition may also contain crystal growth inhibitors. Examples of crystal growth inhibitors include vinyl polymers such as polyvinylpyrrolidone, cellulosic polymers such as hydroxypropyl cellulose, hydroxypropylmethylcellulose, hydroxyethyl cellulose, etc.

In especially preferred aspects of the inventive subject matter, aprepitant-containing formulations are sterile formulations (e.g., prepared via filtration, irradiation, gassing, etc.) and will be bottled into suitable containers, typically for single or multiple independent administrations. Therefore, aprepitant may be present in the container in an amount of 100-200 mg (and most preferably 130 mg), 200-400 mg, 400-600 mg, 600-1000 mg, and even more.

Depending on the particular end user, the aprepitant formulations may be provided as a ready-to-use formulation, i.e., a formulation ready to be administered to the patient without further processing, or as a concentrate that is diluted with a suitable diluent, typically sterile water or other aqueous solvent, e.g., saline. In such case, a kit is provided that includes at least two components, (a) a first container that includes a non-aqueous solvent system comprising a primary co-solvent, a surfactant, and an optional secondary co-solvent, and aprepitant (typically at a concentration of at least 5 mg/ml, more typically at least 9 mg/ml, and most typically 15 mg/ml), and (b) a second container that includes a sterile aqueous diluent in an amount sufficient to dilute the aprepitant to a concentration of at least 5 mg/ml in the final formulation that is ready for administration.

In such concentrates, and as also noted above it is generally preferred that the primary co-solvent and the surfactant are selected such as to form a synergistic mixture with respect to solubilization of aprepitant or present in a synergistic ratio with respect to solubilization of aprepitant. Most typically and where included, the optional secondary co-solvent is present in an amount of equal or less than 30 vol % of the primary co-solvent and the surfactant together.

In further contemplated aspects of the inventive subject matter, formulations can also use or even be exclusively based on complexing agents such as cyclodextrins, and/or by pH adjustment. Suitable complexing agents will thus include any molecule that has capability of forming a complex with aprepitarit to thereby render the aprepitant complexing agent soluble in a suitable solvent. For example, preferred complexing agents include cyclodextrins (e.g., one or more of β-cyclodextrins, HPβ-cyclodextrins, sulfohbutyletherβ-cyclodextrins etc). The cyclodextrins can be used in a molar ratio of 0.05:1 to 10:1, preferably in a molar ratio of 1:30 of cyclodextrin to aprepitant and more preferable in a molar ratio of 1:10 of cyclodextrin to aprepitant.

Most typically, the process of forming complex between aprepitant and a complexing agent involves adding the aprepitant in solid form to a (typically aqueous) solution of the complexing agent, or adding drug and complexing agent together in solid form in aqueous media, or adding a solution of drug prepared using a suitable solvent to the aqueous solution of complexing agent, or adding a solution of drug and complexing agent prepared in a suitable solvent to the aqueous media. Most preferably, a solution of drug is first prepared in a suitable solvent, which is then added to the aqueous solution of complexing agent. The process may further include adjusting the pH of solution using a suitable pH adjusting agent.

In further contemplated processes, aprepitant may also be solubilized in water by pH adjustment. The pH adjustment can be achieved by adding suitable acids such as hydrochloric acid, sulfuric acid, nitric acid, acetic acid, tartaric acid etc. and suitable bases such as sodium hydroxide, potassium hydroxide, ammonium hydroxide etc. Most preferably, the pH is adjusted by addition of acetic acid or tartaric acid and sodium hydroxide. The pH can be adjusted to the desired pH range in order to maintain chemical stability of the drug, preferably in the range of 3 to 8 pH units. Most preferably, the drug is solubilized in an acidic media, for example, acetic acid or tartaric acid followed by addition of a base such as sodium hydroxide. The drug solution thus obtained is then adjusted to final weight or volume by adding water. The final pH can be adjusted in a range from 3 to 8, preferably in a pH range of 4 to 7. Of course, use of a complexing agent may also be enhanced by pH control.

In still further contemplated aspects of the inventive subject matter, pharmaceutical composition of aprepitant can also be prepared as an emulsion, preferably a microemulsion, and most preferably a nanoemulsion. In a particularly preferred embodiment as shown in more detail below, the nanoemulsion is made by dissolving the drug in a suitable oil phase, which can be a pharmaceutically acceptable oil or an organic solvent. The oil phase containing drug is then dispersed in the aqueous external phase mainly composed of water and containing suitable dispersing agents. The emulsion thus obtained can be further homogenized or microfluidized to obtain the desired particle size.

EXAMPLES

The following examples do not limit the scope of applicant's invention but serve as an explanatory tool of applicant's invention. The inventors have tested various methods of solubilizing aprepitant, and these methods may be conceptually grouped into different classes.

Solubilization of Aprepitant by pH

Aprepitant has a pka of 9.7 and does not have sufficient pH dependent solubility in aqueous solutions in physiologically usable pH ranges. Indeed, to be soluble in aqueous solution, a pH of greater than 11.7 is required. However, a formulation with such a high pH is not suitable for injection. Moreover, the instant such a formulation is diluted in blood, the pH will change to about pH 7.4, which will lead to rapid precipitation of the drug. On the other end of the pH spectrum, aprepitant was also found to be soluble in concentrated formic acid, but precipitated almost immediately on twofold dilution with aqueous medium. Similar problems were also encountered where aprepitant is dissolved in a water/ethanol solvent mixture where ethanol is at about 50 volume 9 concentration. Here, dilution that would occur at the injection site would lead to precipitation of the drug and so might lead to chemo-embolism.

Solubilization of Aprepitant by Co-Solvents/Complexing Agent

Example 1

2.9 g of SBE-β-cyclodextrin was dissolved in 5 mL of water. The pH of cyclodextrin solution was adjusted to between 3 to 4, 100 mg of aprepitant was dissolved separately in 3 mL of tetraglycol. Drug solution was gradually added to cyclodextrin solution under constant stirring resulting in a soluble drug-cyclodextrin complex.

Example 2

20 mL of propylene glycol was mixed with 20 mL water followed by addition of 15 mL of glacial acetic acid, 1.0 g of tartaric acid and 5 mL of 2 N hydrochloric acid. 25 mg drug was dissolved separately in 0.5 mL, of tetraglycol. The drug solution is added to the mixture of propylene glycol and acids gradually with constant stirring. pH of solution was adjusted with 10 N NaOH gradually to pH 3 to 4 resulting in, a clear, colorless, particulate free drug solution.

Example 3

3.0 mL of propylene glycol was added to 20 mL water followed by addition of 3.0 g of tartaric acid. 25 mg of drug was dissolved in 0.5 mL of tetraglycol separately. This drug solution was added to the mixture of propylene glycol, tartaric acid and water. pH of this solution was 1.5. The solution was made alkaline by quick addition of 3 mL of 10 N NaOH. The resulting solution had pH of 10 and was clear and colorless with an approximate concentration of 1 mg/mL of aprepitant.

Thus, while the above approaches using complexing agents and/or co-solvents led to a soluble form of aprepitant in at least some instances, concentration of aprepitant is relatively low, and aprepitant tends to precipitate out upon further dilution. As is already known in the art, solubility of aprepitant increases exponentially with increasing concentration of ethanol as shown in Table 1 in the background section. Moreover, maximum allowed concentrations of ethanol in a drug formulation are typically at or below 49 volume %. However, the solubility of aprepitant is still relatively low at or below the allowed concentrations, and only significantly increase when ethanol concentration is ≥50% v/v. Moreover, and as already noted above, an ethanol/water solvent system is not suitable for injection as aprepitant will rapidly precipitate upon dilution at the injection site.

Solubilization of Aprepitant Using Surfactants:

Solubility of aprepitant was tested using different surfactants, and the inventors found that aprepitant solubility was the highest using Polysorbate 80. However, in a typical injectable formulation at Polysorbate 80 concentration of 10% w/v, it would require 7 grams of surfactant, and at Polysorbate 80 concentration of 30% w/v, it would require 9 grams of surfactant to solubilize the aprepitant. Unfortunately, such high quantities of surfactant are entirely unsuitable for injectable formulations (e.g., due to hypersensitivity issues related to polysorbate, foam formation during mixing, etc.). Table 2 below illustrates typical solubility data for aprepitant using water alone as solvent.

TABLE 2

| Surfactant | Concentration (% w/v) | Aprepitant Conc. (mg/mL) |
|---|---|---|
| Cremophor RH 40 | 10 | 1.24 |
|  | 30 | 3.51 |
| Cremophor RH 60 | 10 | 1.24 |
| Poloxamer 188 | 10 | ND |
|  | 30 | 1.24 |
| Polysorbate 80 | 10 | 1.85 |
|  | 30 | 4.42 |

As is readily apparent from Table 2, significant quantities of surfactant are required to achieve moderate concentrations of aprepitant in the water solution.

Solubilization of Aprepitant Using Co-Solvents and Surfactants:

The inventors further tested whether co-solvents (i.e., solvents in addition to water) in combination with surfactants would improve solubility of aprepitant. While numerous co-solvents failed to significantly increase solubility of aprepitant (data not shown), the inventors unexpectedly found that sort-chain (i.e., less than 6 carbon atoms) alcohols, and especially ethanol, synergistically formed with nonionic surfactants, and especially polysorbate 80, a solvent system that substantially improved solubility of aprepitant as compared to solubility of aprepitant in either component alone. In most preferred aspects, a relatively low concentration of nonionic surfactant was chosen in a co-solvent mixture of ethanol and water, and Tables 3-5 below exemplarily illustrate the results of such combination.

More specifically, Table 3 depicts solubility results of aprepitant in water without ethanol at surfactant concentrations noted in the table.

TABLE 3

| Polysorbate 80 Conc. (mg/mL) | Aprepitant Conc. (mg/mL) |
|---|---|
| 11 | 0.179 |
| 22 | 0.308 |
| 44 | 0.505 |

Likewise, Table 4 depicts solubility results of aprepitant in an ethanol/water mixture of (30 vol % EtOH, 70 vol % H2O) at surfactant concentrations noted in the table, and Table 5 depicts solubility results of aprepitant in an ethanol/water mixture of (55 volume % EtOH, 45 vol % H2O) at surfactant concentrations noted in the table.

TABLE 4

| Polysorbate 80 Conc. (mg/mL) | Aprepitant Conc. (mg/mL) |
|---|---|
| — | 0.0232 |
| 11 | 0.560 |
| 44 | 0.793 |

TABLE 5

| Polysorbate 80 Conc. (mg/mL) | Aprepitant Conc. (mg/mL) |
|---|---|
| — | 3.3 |
| 11 | 1.936 |
| 22 | 3.309 |
| 44 | 4.182 |

Pre-Solubilisation of Aprepitant Using Secondary Co-Solvent:

The inventors also tested whether solubility of aprepitant in aqueous polysorbate 80 solutions could be improved when aprepitant was pre-solubilized in a secondary solvent (e.g., dimethylacetamide (DMAC)). For example, when 100 mg aprepitant was solubilized by addition of 200 μL of DMAC, followed by addition of 10 mL of various surfactant solutions, the inventors noted that higher drug solubility was achieved at significantly lower surfactant concentrations as can be seen from Table 6 below. Remarkably, when the inventors directly added 200 μL of DMAC solubilized in 10 mL of water to 100 mg aprepitant (i.e., without surfactant), aprepitant was not detected in the solution phase.

TABLE 6

| Surfactant | Conc. of Polysorbate 80 (% w/v) | Aprepitant Conc. (mg/mL) |
|---|---|---|
| Directly Added | 10 | 1.85 |
|  | 30 | 4.42 |
| Prior Solubilization in DMAC | 5 | 0.85 |
|  | 10 | 2.03 |
|  | 15 | 3.13 |
|  | 20 | 4.35 |
|  | 30 | 4.80 |

Thus, it should be appreciated that the secondary co-solvent in combination with the nonionic surfactant provided for an increased stabilization of dissolved aprepitant that in turn prompted the inventors to investigate various solvent systems, and especially solvent systems that formed an aqueous single phase solvent system from water, a primary co-solvent, a surfactant, and a (optional) secondary co-solvent, wherein the primary co-solvent and the surfactant are present in a synergistic ratio with respect to solubilisation of aprepitant, and wherein the secondary co-solvent is present in an amount of equal or less than 6 volume % of the water and the primary co-solvent together. Moreover, the aprepitant concentration in such systems was typically at least 5 mg/ml. Based on the above results and further considerations (data not shown), the inventors tested various formulations (concentrate and ready-to-use).

Concentrate:

Aprepitant concentrate for injection formulations were prepared by dissolving required quantity of aprepitant in suitable amount of ethanol, and polysorbate 80 were added to the drug and ethanol solution. Typical results and compositions are provided in Table 7 below. Formulations I and II were found to precipitate immediately after dilution with diluent, whereas formulations III, IV, V, VI, and VII were stable (no formation of precipitate) for 24 hours after dilution with diluent. When the water in Formulation I was replaced by PEG 300, a hydrophilic solvent, it was found that it helped inhibit precipitation of aprepitant from the formulation. For commercial use of the concentrate, it is therefore envisioned that the aprepitant solution will be packaged in one vial and that the diluent (e.g., water for injection) is provided in another vial, most typically together as a kit. The aprepitant solution will then be mixed with the diluent and administered within 24 hr of dilution.

TABLE 7

| Formulation | I | II | III | IV | V | VI | VII |
|---|---|---|---|---|---|---|---|
| Concentrate in vial I | | | | | | | |
| Aprepitant | 130 mg | 130 mg | 130 mg | 130 mg | 130 mg | 130 mg | 130 mg |
| Polysorbate 80 | 0.25 g | 0.5 g | 0.5 g | 0.25 g | 0.25 g | 0.3 g | 0.3 g |
| Ethanol | 10 ml | 10 ml | 12.5 mL | 12.5 ml | 10 ml | 11 ml | 11 ml |
| PEG 300 | — | — | — | — | 2 ml | 2 ml | 3 ml |
| Water for Injection in vial II | | | | | | | |
| Diluent Water for Injection | 12.5 ml | 12.5 ml | 10 mL | 10 ml | 8 ml | 10 ml | 9 ml |

Ready-to-Use Aprepitant Solutions for Injection:

Exemplary ready-to-use aprepitant solutions for injection were prepared by dissolving a required quantity of aprepitant in some examples with dimethylacetamide, or in suitable amount of ethanol. Subsequently added were polysorbate 80 and PEG as indicated, followed by addition of water for injection. The results are presented in Tables 8-9 below. Notably, PEG 300 used at lower concentration was able to solubilize aprepitant, but led to drug precipitation at higher concentrations.

TABLE 8

| Formulation | VIII | IX | X | XI | XII |
|---|---|---|---|---|---|
| Aprepitant (mg) | 130 | 130 | 130 | 130 | 130 |
| Polysorbate 80 (g) | 3 | 2 | 1.5 | 1 | 0.5 |
| Ethanol (ml) | 12.57 | 12.57 | 12.57 | 12.57 | 12.57 |
| DMAc (µL) | 200 | 200 | 200 | 200 | 200 |
| PEG 300 (ml) | — | — | — | — | 8 |
| Water qs (mL) | 30 | 25 | 30 | 23 | 50 |
| Stability 40 Deg/75% RH | Stable | Unstable | Unstable | Stable | Unstable |

TABLE 9

| Formulation | XIII | XIV | XV | XVI | XVII | XVIII |
|---|---|---|---|---|---|---|
| Aprepitant (mg) | 130 | 130 | 130 | 130 | 130 | 130 |
| Polysorbate 80 (g) | 0.75 | 0.5 | 0.5 | 0.5 | 0.5 | 0.25 |
| Ethanol (ml) | 12.57 | 12.57 | 12.57 | 12.57 | 12.57 | 12.57 |
| DMAc (µL) | 200 | 200 | — | — | — | 200 |
| PEG 300 (ml) | — | — | 1 | 2 | 5 | — |
| Water qs (mL) | 23 | 23 | 23 | 23 | 23 | 23 |
| Stability 40 Deg/75% RH | Stable | 1 Month | 2 Months | 1 Month | Unstable | 10 Hours |

Table 10 below shows exemplary stability data for exemplary formulations XV and Xv tested under conditions as noted in the table. As will be readily appreciated, aprepitant remained dissolved and remained chemically stable in solution for extended periods of time.

TABLE 10

| Formulation | Temperature | Time | Assay |
|---|---|---|---|
| XVI | 25 Deg/60% RH | Initial | 98.6 |
| | | 1 Week | 98.0 |
| | | 2 Week | 97.8 |
| | | 1 Month | 97.9 |
| | 40 Deg/75% RH | 1 Week | 98.5 |
| | | 2 Weeks | 98.1 |
| | | 1 Month | 98.2 |
| XV | 25 Deg/60% RH | Initial | NT |
| | | 1 Week | 97.9 |
| | | 3 Weeks | 98.6 |

TABLE 10-continued

| Formulation | Temperature | Time | Assay |
|---|---|---|---|
| | 25 Deg/60% RH | 1 Week | 97.9 |
| | | 3 Weeks | 97.2 |

(NT: Not tested)

Therefore, it is contemplated that the formulations of the present invention will be in a container in a volume suitable for at least one administration (typically at a dose of 130 mg aprepitant per administration). However, it should also be appreciated that the container may include sufficient quantities of aprepitant suitable for multiple independent administrations, for example, 2, 3, 4, 5, and even more independent administrations.

Emulsion Formulations:

As is well established, aprepitant is substantially insoluble in both oil and water. However, the inventors discovered that various emulsion formulations could be prepared from which aprepitant did not precipitate.

Formulation I:

Glycerin was weighed in the compounding vessel. Water (80 mL) was added to the vessel and heated to 70° C., Soybean oil (13 mL) was also heated to 70° C. Aprepitant (130 mg) was solubilized in 200 µL, of N,N'-Dimethylacetamide and added to the oil phase. The aqueous phase was added to the oil phase and a crude emulsion was formed using a high speed homogenizer, and the crude emulsion was then passed through a high pressure homogenizer to form the final emulsion as shown in Table 11.

TABLE 11

| Compound | Quantity |
|---|---|
| Aprepitant | 130 mg |
| DMAC | 200 µL |
| Soybean oil | 13 mL |
| Lipoid E80 | 1.56 grams |
| Glycerin | 2.86 grams |
| Water q.s | 130 mL |

Formulation II:

Glycerin was weighed in the compounding vessel. Water (80 mL) was added to the vessel and heated to 70° C. Soybean oil (13 mL) was also heated to 70° C. Aprepitant (130 mg) was dispersed in the oil phase. The aqueous phase was added to the oil phase and a crude emulsion was formed using a high speed homogenizer, and the crude emulsion was then passed through a high pressure homogenizer to form the final emulsion as shown in Table 12.

TABLE 12

| Compound | Quantity |
|---|---|
| Aprepitant | 130 mg |
| Soybean oil | 13 mL |
| Lipoid E80 | 1.56 grams |
| Glycerin | 2.86 grams |
| Water q.s | 130 mL |

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A sterile liquid formulation of aprepitant for injection, comprising:
    an aqueous single phase solvent system comprising water, a primary co-solvent, a surfactant, and a secondary co-solvent;
        wherein the primary co-solvent is a short-chain alcohol;
        wherein the surfactant is a non-ionic surfactant polyoxyethylene glycol sorbitan alkyl esters wherein the primary co-solvent and the surfactant are present in a synergistic ratio with respect to solubilisation of aprepitant;
        wherein the secondary co-solvent is present in an amount of equal or less than volume % of the water and the primary co-solvent together; and
    aprepitant at a concentration of at least 5 mg/ml.
2. The sterile liquid formulation of claim 1, wherein the short-chain alcohol is ethanol.
3. The sterile liquid formulation of claim 1, wherein the non-ionic polyoxyethylene glycol sorbitan alkyl esters surfactant is a polysorbate.
4. The sterile liquid formulation of claim 1, wherein the secondary co-solvent is a short-chain polyethylene glycol or dimethylacetamide.
5. The sterile liquid formulation of claim 4, wherein the secondary co-solvent is a short-chain polyethylene glycol and is present in an amount of equal or less than 3 volume %.
6. The sterile liquid formulation of claim 4, wherein the secondary co-solvent is dimethylacetamide and is present in an amount of equal or less than 1 volume %.
7. The sterile liquid formulation of claim 1, wherein the primary co-solvent is ethanol, the secondary co-solvent is a short-chain polyethylene glycol or dimethylacetamide, and wherein the surfactant is a polysorbate.
8. The sterile liquid formulation of claim 1, wherein the secondary co-solvent is omitted from the sterile liquid formulation.
9. A kit for preparation of a sterile liquid formulation of aprepitant for injection, the kit comprising:
    (a) a first container that includes a solvent system comprising a primary co-solvent, a surfactant, and an optional secondary co-solvent;
        wherein the primary co-solvent is a short-chain alcohol;
        wherein the surfactant is a non-ionic surfactant polyoxyethylene glycol sorbitan alkyl esters wherein the primary co-solvent and the surfactant are present in a synergistic ratio with respect to solubilization of aprepitant;
        wherein the optional secondary co-solvent is present in an amount of equal or less than 30 vol % of the primary co-solvent and the surfactant together;
        aprepitant at a concentration of at least 9 mg/ml;
    (b) a second container that includes a sterile aqueous diluent in an amount sufficient to dilute the aprepitant to a concentration of at least 5 mg/ml; and
    wherein the non-aqueous solvent system and the sterile aqueous diluent are present in an amount such that the aprepitant at the concentration of at least 5 mg/ml is completely soluble and stable in the sterile liquid formulation.
10. The kit of claim 9 wherein the secondary co-solvent is a short-chain polyethylene glycol or dimethylacetamide.
11. The kit of claim 9 wherein the sterile aqueous diluent is water.
12. A method of increasing solubility and stability of aprepitant in an aqueous solution, the method comprising:
    preparing an aqueous single phase solvent system comprising water, a primary co-solvent, and a surfactant, wherein the primary co-solvent and the surfactant are present in a synergistic ratio with respect to solubilization of aprepitant;
        wherein the primary co-solvent is a short-chain alcohol; and
        wherein the surfactant is a non-ionic surfactant polyoxyethylene glycol sorbitan alkyl esters;
    dissolving aprepitant in a secondary co-solvent to form a concentrated aprepitant solution;
    combining the concentrated aprepitant solution with the aqueous single phase solvent system to thereby form an aprepitant formulation with increased solubility and stability for aprepitant.
13. The method of claim 12 wherein the secondary co-solvent is a short-chain polyethylene glycol or dimethylacetamide.

14. The method of claim 12 wherein aprepitant formulation contains at least 5 mg/ml aprepitant.

15. The method of claim 12 wherein aprepitant in the aprepitant formulation remains in solution for at least one month when stored at 40° C. and 75% relative humidity.

* * * * *